US010258932B2

(12) United States Patent
Birss et al.

(10) Patent No.: US 10,258,932 B2
(45) Date of Patent: Apr. 16, 2019

(54) POROUS CARBON FILMS

(71) Applicant: UTI LIMITED PARTNERSHIP, Calgary (CA)

(72) Inventors: Viola Birss, Calgary (CA); Xiaoan Li, Calgary (CA); Dustin Banham, West Vancouver (CA); Daniel Y. Kwok, Cochrane (CA)

(73) Assignee: UTI Limited Partnership, Calgary, Alberta (CA)

(*) Notice: Subject to any disclaimer, the term of this patent is extended or adjusted under 35 U.S.C. 154(b) by 148 days.

(21) Appl. No.: 15/124,847

(22) PCT Filed: Mar. 11, 2015

(86) PCT No.: PCT/CA2015/000156
§ 371 (c)(1),
(2) Date: Sep. 9, 2016

(87) PCT Pub. No.: WO2015/135069
PCT Pub. Date: Sep. 17, 2015

(65) Prior Publication Data
US 2017/0014780 A1 Jan. 19, 2017

Related U.S. Application Data

(60) Provisional application No. 61/950,965, filed on Mar. 11, 2014.

(51) Int. Cl.
*H01M 4/86* (2006.01)
*H01M 4/88* (2006.01)
(Continued)

(52) U.S. Cl.
CPC .......... *B01D 71/021* (2013.01); *B01J 20/103* (2013.01); *B01J 20/205* (2013.01);
(Continued)

(58) Field of Classification Search
CPC .. B01D 2325/02; B01D 71/021; B01J 20/103; B01J 20/3204; B01J 20/324;
(Continued)

(56) References Cited

U.S. PATENT DOCUMENTS

| 4,919,860 A | 4/1990 | Schindler et al. |
| 5,798,188 A | 8/1998 | Mukohyama et al. |

(Continued)

FOREIGN PATENT DOCUMENTS

| WO | WO 2005/006471 | 1/2005 |
| WO | WO 2010/019221 | 2/2010 |

(Continued)

OTHER PUBLICATIONS

Adelhelm et al. On the use of mesophase pitch for the preparation of hierarchical porous carbon monoliths by nanocasting. Sci. Technol. Adv. Mater., Feb. 2012, 13, 015010.

(Continued)

*Primary Examiner* — Stella K Yi
(74) *Attorney, Agent, or Firm* — Leydig, Voit & Mayer, Ltd.

(57) ABSTRACT

Self-supporting or supported porous carbon films, including nanoporous carbon films, are provided. The porous carbon films comprise an open network of interconnected pores. Methods for making porous carbon films are also provided. One synthesis method includes formation of a synthesis mixture comprising particles of an inorganic material, a carbon precursor material and water, forming a layer of the synthesis mixture on a substrate and heat treating the film to convert the carbon precursor to carbon.

21 Claims, 6 Drawing Sheets

(51) Int. Cl.
| | | |
|---|---|---|
| H01M 4/90 | (2006.01) | |
| H01M 4/92 | (2006.01) | |
| H01M 4/96 | (2006.01) | |
| B01D 71/02 | (2006.01) | |
| B01J 20/10 | (2006.01) | |
| B01J 20/20 | (2006.01) | |
| B01J 20/28 | (2006.01) | |
| B01J 20/32 | (2006.01) | |
| C01B 32/05 | (2017.01) | |
| C12N 11/14 | (2006.01) | |
| H01M 8/0234 | (2016.01) | |
| H01M 8/0243 | (2016.01) | |

(52) U.S. Cl.
CPC ..... *B01J 20/28019* (2013.01); *B01J 20/3204* (2013.01); *B01J 20/324* (2013.01); *B01J 20/3248* (2013.01); *B01J 20/3293* (2013.01); *C01B 32/05* (2017.08); *C12N 11/14* (2013.01); *H01M 4/8605* (2013.01); *H01M 4/8807* (2013.01); *H01M 4/9016* (2013.01); *H01M 4/9041* (2013.01); *H01M 4/9083* (2013.01); *H01M 4/926* (2013.01); *H01M 4/96* (2013.01); *H01M 8/0234* (2013.01); *H01M 8/0243* (2013.01); *B01D 2325/02* (2013.01); *C01P 2006/12* (2013.01); *C01P 2006/16* (2013.01)

(58) Field of Classification Search
CPC ........... H01M 8/0234; B29C 66/72323; B29C 67/20; B29C 2043/3668; B29C 44/00
See application file for complete search history.

(56) References Cited

U.S. PATENT DOCUMENTS

| | | | |
|---|---|---|---|
| 6,503,653 | B2 | 1/2003 | Rock |
| 7,056,455 | B2 | 6/2006 | Matyjaszewski et al. |
| 7,622,217 | B2 | 11/2009 | Debe et al. |
| 7,803,345 | B2 | 9/2010 | Leis et al. |
| 7,993,797 | B2 | 8/2011 | Salguero et al. |
| 8,164,881 | B2 | 4/2012 | Hu et al. |
| 2002/0132159 | A1 | 9/2002 | Ohya et al. |
| 2005/0260118 | A1 | 11/2005 | Lu et al. |
| 2009/0233792 | A1* | 9/2009 | Kimijima ........... B01J 67/0067 502/402 |
| 2010/0167105 | A1 | 7/2010 | Finsterwalder et al. |
| 2012/0148473 | A1 | 6/2012 | Kramarenko |
| 2012/0219488 | A1 | 8/2012 | Dash |
| 2017/0014780 | A1 | 1/2017 | Birss et al. |
| 2017/0200954 | A1 | 7/2017 | Birss et al. |

FOREIGN PATENT DOCUMENTS

| | | |
|---|---|---|
| WO | WO 2011/135451 | 11/2011 |
| WO | WO 2013/011146 | 1/2013 |
| WO | WO 2015/135069 A1 | 9/2015 |

OTHER PUBLICATIONS

Adora et al. Electrochemical deposition of platinum nanoparticles on carbon: A study by standard and anomalous X-ray diffraction. Chemphyschem 2004, 5, 1178-1184.

Antoine et al. In situ electrochemical deposition of Pt nanoparticles on carbon and inside Nafion. Electrochemical and Solid State Letters 2001, 4(5), A55-A58.

Antolini. Carbon supports for low-temperature fuel cell catalysts. Applied Catalysis B: Environmental 2009, 88, 1-24.

Antolini. Formation of carbon-supported PtM alloys for low temperature fuel cells: a review. Materials Chemistry and Physics 2003, 78, 563-573.

Banham et al. Bimodal, templated mesoporous carbons for capacitor applications. Carbon 2010;48(4):1056-63.

Banham et al. Effect of Pt-loaded carbon support nanostructure on oxygen reduction catalysis. J Power Sources 2011;196(13):5438-45.

Banham et al. First time investigation of Pt nanocatalysts deposited inside carbon mesopores of controlled length and diameter. Journal of Materials Chemistry Jan. 2012, 22, 7164-7171.

Banham et al. Effect of carbon support nanostructure on the oxygen reduction activity of Pt/C catalysts. J Mater Chem A Jan. 2013;1(8):2812-20.

Bitter et al. Synthesis of Highly Loaded Highly Dispersed Nickel on Carbon Nanofibers by Homogeneous Deposition—Precipitation. Catalysis Letters 2003, 89, 1-2, 139-142.

Cai et al. A novel polyaniline/mesoporous carbon nano-composite electrode for asymmetric supercapacitor. Chinese Chemical Letters 2010, 21, 1509-1512.

Chang et al. Synthesis and characterization of mesoporous carbon for fuel cell applications. Journal of Materials Chemistry 2007, 17, 3078-3088.

Chen et al. Polyaniline-deposited porous carbon electrode for supercapacitor. Electrochimica Acta 2003, 48, 641-649.

Cheng et al. Carbon-supported manganese oxide nanocatalysts for rechargeable lithium-air batteries. Journal of Power Sources 2010, 195, 1370-1374.

Chicharro et al. Tape casting of graphite material: A new electrochemical sensor. Electroanalysis 2006;18(16):1614-9.

Chmiola et al. Monolithic Carbide-Derived Carbon Films for Micro-Supercapacitors. Science 2010, 328(5977):480-3.

Choi et al. Nano-structured Pt-Cr anode catalyst over carbon support, for direct methanol fuel cell. Journal of Power Sources 2006, 156, 466-471.

Coleman et al. Small but strong: A review of the mechanical properties of carbon nanotube-polymer composites. Carbon 2006, 44, 1624-1652.

Darmstadt et al. Surface chemistry of ordered mesoporous carbons. Carbon 2002, 40, 2673-2683.

De Jong et al. Carbon Nanofibers: Catalytic Synthesis and Applications. Catalysis Reviews, Science and Engineering 2000, 42(4), 481-510.

El Sawy et al. A Comparative Study of the Electrodeposition of Nanoporous Ir and Pt Thin Films. Journal of the Electrochemical Society Jul. 2013, 160, D386-D393.

Fitzer et al. Recommended terminology for the description of carbon as a solid (IUPAC Recommendations 1995), Pure Appl. Chem., 1995, vol. 67(3), 473-506.

Flandrois et al. Carbon materials for lithium-ion rechargeable batteries. Carbon 1999, 37, 165-180.

Frampton. Effects of Controlled Exposure to Ultrafine Carbon Particles in Healthy and Asthmatic People. Synopsis of Research Report 2004, 126, Health Effects Institute.

Grigoriev et al. Evaluation of carbon-supported Pt and Pd nanoparticles for the hydrogen evolution reaction in PEM water electrolysers. Journal of Power Sources 2008, 177, 281-285.

Han et al. Simple silica-particle template synthesis of mesoporous carbons. Chem Commun. 1999, 1955-1956.

Han et al. Direct Preparation of Nanoporous Carbon by Nanocasting. J. Am. Chem. Soc., 2003, 125, 3444-34445.

Haug et al. Increasing proton exchange membrane fuel cell catalyst effectiveness through sputter deposition. Journal of the Electrochemical Society 2002, 149(3), A280-A287.

Hilal et al. A comprehensive review of nanofiltration membranes:Treatment, pretreatment, modelling, and atomic force microscopy. Desalination 2004;170(3):281-308.

Hu et al. Processing of an aqueous tape casting of mesocarbon microbeads for high-performance carbonaceous laminations. Carbon 2003;41(12):2285-93.

Huang, J.; Sumpter, B. G.; Meunier, V. A Universal Model for Nanoporous Carbon Supercapacitors Applicable to Diverse Pore Regimes, Carbon Materials, and Electrolytes. Chemistry—A European Journal 2008, 14, 6614-6626.

Huang. Carbon black filled conducting polymers and polymer blends. Advances in Polymer Technology 2002, 21, 299-313.

(56) References Cited

OTHER PUBLICATIONS

Inagaki et al. Morphology and pore control in carbon materials via templating. RSC Advances, 2011, 1, 1620-1640.
International Search Report and Written Opinion corresponding to International Application No. PCT/CA 2015/000156, dated Jun. 9, 2015, 12 pages.
Jache et al. Towards commercial products by nanocasting: characterization and lithium insertion properties of carbons with a macroporous, interconnected pore structure. J. Mater. Chem. 2012, 22, 10787.
Kim et al. Functionalized Multiwall Carbon Nanotube/Gold Nanoparticle Composites. Langmuir 2004, 20, 8239-8242.
Kim et al. Ordered macroporous platinum electrode and enhanced mass transfer in fuel cells using inverse opal structure. Nature Communications Aug. 2013, 4, 1-9.
Kimijima et al. Preparation of a self-standing mesoporous carbon membrane with perpendicularly-ordered pore structures. Chemical Communications 2008, (44):5809-11.
Korkut et al. High Surface Area Tapes Produced with Functionalized Graphene. Acs Nano 2011, 5(6):5214-22.
Labiano et al. Impact of Homopolymer Pore Expander on the Morphology of Mesoporous Carbon Films Using Organic-Organic Self-Assembly. Journal of Physical Chemistry C Feb. 2012;116(10):6038-46.
Lee et al. Synthesis of new nanoporous carbon materials using nanostructured silica materials as templates. Journal of Materials Chemistry 2004, 14, 478-486.
Li et al. Colloid-Imprinted Carbons as Stationary Phases for Reversed-Phase Liquid Chromatography. Analytical Chemistry 2004, 76, 5479-5485.
Liang et al. Synthesis of a large-scale highly ordered porous carbon film by self-assembly of block copolymers. Angewandte Chemie—International Edition 2004, 43(43):5785-9.
Lin et al. Well-Ordered Mesoporous Carbon Thin Film with Perpendicular Channels: Application to Direct Methanol Fuel Cell. The Journal of Physical Chemistry C 2008, 112, 867-873.
Liu et al. Sulfonated ordered mesoporous carbon for catalytic preparation of biodiesel. Carbon 2008, 46, 1664-1669.
Mahurin et al. Ammonia-activated mesoporous carbon membranes for gas separations. Journal of Membrane Science 2011, 368(1-2):41-7.
Medalia. Electrical Conduction in Carbon Black Composites. Rubber Chemistry and Technology 1986, 59, 432-454.
Mehta et al. Review and analysis of PEM fuel cell design and manufacturing. Journal of Power Sources 2003, 114, 32-53.
Mochida et al. Preparation, Structure and Application of Mesophase Pitches Prepared from Aromatic Hydrocarbons Using $HF/BF_3$ as Catalysts. TANSO 1992, 155:370-378.
Moriguchi et al. Colloidal crystal-templated porous carbon as a high performance electrical double-layer capacitor material. Electrochemical and Solid State Letters 2004, 7(8):A221-A223.
Oh et al. Nanoporous activated carbon cloth for capacitive deionization of aqueous solution. Thin Solid Films 2006, 515, 220-225.
Ohzuku et al. Formation of Lithium-Graphite Intercalation Compounds in Nonaqueous Electrolytes and Their Application as a Negative Electrode for a Lithium Ion (Shuttlecock) Cell. Journal of the Electrochemical Society 1993, 140(9), 2490-2498.
Pandolfo et al. Carbon properties and their role in supercapacitors. Journal of Power Sources 2006, 157, 11-27.
Pang et al. Silica-Templated Continuous Mesoporous Carbon Films by a Spin-Coating Technique. Adv. Mater. 2004, vol. 16, No. 11, pp. 884-886.
Pantea et al. Electrical conductivity of conductive carbon blacks: influence of surface chemistry and topology. Applied Surface Science 2003, 217, 181-193.
Pantea et al. Electrical conductivity of thermal carbon blacks: Influence of surface chemistry. Carbon 2001, 39, 1147-1158.
Pei et al. Oxygen reduction activity dependence on the mesoporous structure of imprinted carbon supports. Electrochem Commun 2010, 12(11):1666-9.
Rahimi et al. CMK-3 nanoporous carbon as a new fiber coating for solid-phase microextraction coupled to gas chromatography—mass spectrometry. Analytica Chimica Acta 2011, 695, 58-62.
Rodriguez. A review of catalytically grown carbon nanofibers. Journal of Materials Research 1993, 8, 3233-3250.
Ryoo et al. Synthesis of Highly Ordered Carbon Molecular Sieves via Template-Mediated Structural Transformation. The Journal of Physical Chemistry B 1999, 103, 7743-7746.
Sakintuna et al. Templated Porous Carbons: A Review Article. Industrial & Engineering Chemistry Research 2005, 44, 2893-2902.
Siegal et al. Nanoporous-carbon films for microsensor preconcentrators. Applied Physics Letters 2002, 80(21):3940-2.
Song et al. Challenges in Fabrication of Mesoporous Carbon Films with Ordered Cylindrical Pores via Phenolic Oligomer Self-Assembly with Triblock Copolymers. Acs Nano 2010, 4(1):189-98.
Tanaka et al. Fabrication of continuous mesoporous carbon films with face-centered orthorhombic symmetry through a soft templating pathway. Journal of Materials Chemistry 2007, 17(34):3639-45.
Tao et al. Recent progress in the synthesis and applications of nanoporous carbon films. J. Mater. Chem., 2011, 21, 313-323.
Thostenson, E. T.; Ren, Z.; Chou, T.-W. Advances in the science and technology of carbon nanotubes and their composites: a review. Composites Science and Technology 2001, 61, 1899-1912.
Tibbetts et al. A review of the fabrication and properties of vapor-grown carbon nanofiber/polymer composites. Composites Science and Technology 2007, 67, 1709-1718.
Vairavapandian et al. Preparation and modification of carbon nanotubes: Review of recent advances and applications in catalysis and sensing. Analytica Chimica Acta 2008, 626, 119-129.
Wang et al. Carbon Nanotube-Based Thin Films: Synthesis and Properties, In: *Carbon Nanotubes—Synthesis, Characterization, Applications,* Editor Dr. S. Yellampalli, Published by Intech, 2011, 30 pages.
Wang. Carbon-Nanotube Based Electrochemical Biosensors: A Review. Electroanalysis 2005, 17(1), 7-14.
Wang et al. Synthesis of ordered mesoporous boron-containing carbon films and their corrosion behavior in simulated proton exchange membrane fuel cells environment. Journal of Power Sources Apr. 2012, 212, 1-12.
Wei et al. Mass Transport and Electrode Accessibility Through Periodic Self-Assembled Nanoporous Silica Thin Films. Langmuir 2007, 23, 5689-5699.
White et al. Restoration of Large Damage Volumes in Polymers. Science May 2014, 344, 620-623.
Wickramaratne et al. Graphitic Mesoporous Carbons with Embedded Prussian Blue-Derived Iron Oxide Nanoparticles Synthesized by Soft Templating and Low-Temperature Graphitization. Chemistry of Materials Jun. 2013, 25, 2803-2811.
Wildgoose et al. Metal Nanoparticles and Related Materials Supported on Carbon Nanotubes: Methods and Applications. Small 2006, 2, 182-193.
Wu et al. Carbon anode materials for lithium ion batteries. Journal of Power Sources 2003, 114, 228-236.
Ye et al. Two-dimensionally patterned nanostructures based on monolayer colloidal crystals: Controllable fabrication, assembly, and applications. Nano Today 2011, 6(6):608-31.
Yu et al. Ordered uniform porous carbon by carbonization of sugars. Carbon, 2001, 39, 1421-1446.
Yue et al. Nanoparticle and Nanoporous Carbon Adsorbents for Removal of Trace Organic Contaminants from Water. J Nanopart Res 2005, 7, 477-487.
Zhi et al. Carbonization of disclike molecules in porous alumina membranes: Toward carbon nanotubes with controlled graphene-layer orientation. Angewandte Chemie—International Edition 2005, 44(14):2120-3.
Zhu et al. Applications of carbon materials in photovoltaic solar cells. Solar Energy Materials and Solar Cells 2009, 93, 1461-1470.
Hayashi et al. (2008) "Preparation of Pt/mesoporous carbon (MC) electrode catalyst and its reactivity toward oxygen reduction," Electrochim. Acta. 53(21):6117-25.
Kao et al. (2007) "Silica template synthesis of ordered mesoporous carbon thick films with 35-nm pore size from mesophase pitch solution," Mater. Lett. 62(4-5):695-698.

(56) References Cited

OTHER PUBLICATIONS

Liu et al. (2005) "Carbon-supported Pt nanoparticles as catalysts for proton exchange membrane fuel cells," J. Power Sources. 139(1-2):73-8.

Moreira et al. (2004) "Synthesis, characterization and application of a Pd/Vulcan and Pd/C catalyst in a PEM fuel cell," Int. J. Hydrogen Energy. 29(9):915-20.

Wang et al. (1994) "Ultrathin Porous Carbon Films as Amperometric Transducers for Biocatalytic Sensors," Anal. Chem. 66(13):1988-1992.

Wang et al. (2004) "Structure and performance of different types of agglomerates in cathode catalyst layers of PEM fuel cells," J. Electroanal. Chem. 573(1):61-9.

Wang et al. (2006) "Micro-porous layer with composite carbon black for PEM fuel cells," Electrochimica Acta. 51(23):4909-4915.

\* cited by examiner

POROUS CARBON FILMS

CROSS-REFERENCE TO RELATED APPLICATIONS

This application is a 35 U.S.C. § 371 filing of International Application No. PCT/CA2015/000156, filed Mar. 11, 2015, which claims the benefit of priority of U.S. Provisional Application No. 61/950,965, filed Mar. 11, 2014, each of which is hereby incorporated by reference herein in its entirety.

BACKGROUND

Carbonaceous materials with nanoscopic structures have been studied extensively and used widely because of their low specific gravity, good electrical conductivity, high surface area, ability to be readily surface-modified, as well as the feasibility of large-scale production. Examples of these materials are carbon black, carbon nanotubes, carbon nanofibers, ordered mesoporous carbons, and so on. Porous colloid imprinted carbon (CIC) powders have also been prepared with a narrow pore size distribution and three-dimensionally connected nanopores, verified by nitrogen adsorption isotherms and three-dimensional transmission electron microscopy (3D-TEM) [1, 2]. These nanomaterials are being used in many applications, such as electrochemical devices, including batteries, capacitors, and fuel cells.

However, most of these carbon materials are available only in powder form, which limits their applications. Variation in the orientation or alignment of the individual nanoporous carbon particles may affect mass transport through the nanopores and also make product properties irreproducible. In addition, use of carbon powders has associated health concerns, since particulates are known to be an increasing problem.

In some cases, carbon powders can be obtained already bound together with a polymer. For example, Pt-loaded nanoporous carbon can be bound with a polymer to serve as the catalyst layer in polymer electrolyte membrane fuel cells (PEMFCs). However, these polymeric binders may negatively affect the conductivity or mass transfer through the carbon powders or may contaminate them, thus lowering their performance. To handle this problem, electrically conducting polymers (e.g., polyaniline) are used as a binder in supercapacitors to improve the conductivity between carbon particles. However, the polymeric phase may narrow the pathways for electrolyte ions, which is expected to decrease the charge/discharge rate of the capacitors.

In the past decade, a number of techniques have been developed to fabricate nanoporous carbonaceous materials in bulk form, e.g., carbon gels or monoliths, carbon films [3-6], carbon tapes [7], carbon cloth, etc. Of these, nanoporous carbon films (NCFs) are very promising for various applications, including applications as electrodes, adsorbents, catalysts, separation materials, and sensors. NCFs can be prepared via hard-template or soft-template methods, filtration, pyrolysis of polymer precursors, chemical or physical vapor deposition, and other chemical and physical methods [6, 8-14]. These techniques can provide NCFs with excellent properties, but they also face one or more of the following problems: high cost of raw materials, complicated/tedious or time-consuming preparation process, low mechanical strength, low electrical conductivity, low porosity, non-continuous nano-pores, uncontrolled orientation of the pores, and challenges with mass production.

BRIEF SUMMARY OF THE INVENTION

The invention provides porous carbon-based films, including nanoporous carbon-based films, nanoporous carbon films (NCFs), and methods for synthesis thereof. Nanoporous carbon-based films produced by the methods of the present invention have a variety of applications including, but not limited to, batteries, flexible batteries, electrodes, sensors, fuel cells, chromatographic materials and filtration.

In an aspect, the films have a thickness substantially less than their lateral dimensions. In an embodiment, the lateral dimensions are of macroscopic dimensions (e.g., greater than 1 mm or 1 cm), while the thickness dimension is in the nanoscale or microscale. In an embodiment, the porous carbon-based films are freestanding and are not attached to a support material or backing. In an embodiment, a freestanding film is sheet of material which is self-supporting. For example, a self-supporting film is capable of supporting itself in the absence of a support material or backing. In an embodiment the self-supporting sheet of material has sufficient mechanical strength that it can be readily transferred without being substantially damaged. In an embodiment, the porous carbon-based films are flexible enough to be rolled or bent without visibly cracking or breaking the film.

In an embodiment, the carbon-based films comprise carbonaceous regions which define the pore space within the film. In an embodiment, the pores within the film form a three-dimensionally interconnected network of pores. In an embodiment, the film comprises nanopores. In an embodiment, the film comprises an open network of interconnected pores, the network comprising pores having a size from 2 nm to 100 nm, from 5 nm to 100 nm, from 10 nm to 100 nm, from 10 nm to 50 nm or from 15 to 40 nm. In a further embodiment, the film comprises macropores, the macropores having a size greater than 100 nm and less than one micrometer. In yet a further embodiment, the film comprises pores having a size less than 2 nm. In a further embodiment, the network further comprises pores having a size from 0.1 μm to 100 μm. In an embodiment, the film comprises an open network of interconnected pores, the network comprising pores having a diameter greater than 100 nm and less than or equal to 100 μm. In an embodiment, the film comprises pores having a wide range of size distribution, e.g., from <2 nm to >100 μm. In an embodiment, a gradient in porosity is formed across the thickness of the film.

In different embodiments, the synthesis methods, properties, modification, and applications for nanoporous carbon films (NCF) described herein are also applicable for carbon films with pores larger than 100 nm or smaller than 2 nm. In an embodiment, carbon films with pores larger than 100 nm or smaller than 2 nm can be produced using the methods described herein. In a further embodiment, carbon films with pores larger than 100 nm are formed by using a non-aqueous synthesis mixture.

In an embodiment, the method for porous carbon-based film synthesis comprises the steps of forming a mixture comprising particles of an inorganic material, a carbon precursor material and water, forming a layer of the mixture on a substrate, removing water from the layer to form a film, heating the film to convert the carbon precursor in the film to carbon, thereby forming a composite film comprising carbon and particulate material and removing particulate material from the composite film to form a porous carbon-based film. In an embodiment, the particulate material serves as a sacrificial template for pores in the film. In an embodiment, the film is removed from the substrate prior to carbonization of the film. As used herein, a carbon-based film is predominately carbon. In an embodiment, the amount of elements other than carbon in the film is less than 20%, 10 wt %, 5 wt %, 2 wt % or 1 wt % and the film may be termed a porous carbon film. When the porous carbon film comprises pores in the size range from 2 nm to 100 nm, the porous carbon film may be termed a nanoporous carbon film (NCF). The mixture is also referred to herein as a synthesis mixture. In an embodiment, the water content of the synthesis mixture is from 1% to 99% in weight or 40% to 90% in weight. In a further embodiment, the synthesis mixture comprises a liquid other than water.

The aqueous synthesis mixture, comprising an inorganic particulate material, a carbon precursor material and water, may also be termed an ink. In an embodiment, the template material can be any inorganic material that does not react with carbon and its precursor during the preparation process. In an embodiment, the template material is metal-oxide-based. In embodiments, the metal-oxide based particles are suspensible in aqueous solutions or are suspensible in the presence of a stabilizing agent such as an ionic stabilizing agent. Suitable metal-oxide based materials include, but are not limited to, silica based materials, alumina based materials, titania based materials and magnesia based materials. Suitable silica-based templates include, but are not limited to, colloidal silica. In embodiments, the average particle size of the particles of inorganic material is from 2 nm to 100 nm, 5 nm to 50 nm, 5 nm to 25 nm, 25 nm to 50 nm, or 50 to 100 nm. In an embodiment, particles with a size out of the nanosize ranges will result in carbon films with pores size larger than 100 nm or smaller than 2 nm, correspondingly. In further embodiments, the average particle size of the inorganic particles is from 0.5 nm to 100 µm, from 0.5 nm to less than 2 nm, or from greater than 100 nm to 10 µm. A variety of inorganic material particle shapes, including spherical, are suitable for use with the methods of the invention. Various inorganic material nano-structures are also suitable for use with the methods of the invention.

Suitable carbon precursors, include, but are not limited to, mesophase pitch (MP). In an embodiment, a mesophase pitch carbon precursor is selected from the group consisting of naphthalene-based pitch, coal-based pitch, oil-based pitch, and other-source-based pitches. Other suitable sources of carbon include, but are not limited to, carbohydrates (e.g., sucrose), polymers (e.g., phenol formaldehyde resins), oligomers, alcohols and polycyclic aromatic hydrocarbons (e.g., anthracene and naphthalene). In embodiments, the mass ratio of carbon precursor to inorganic particulate materials is from 1/20 to 2/1, from 1/20 to 1/5 or from 1/10 to 1/1. In embodiments, within the synthesis mixture, the mass ratio of MP to colloidal silica is from 1/20 to 2/1, from 1/20 to 1/5, or from 1/10 to 1/2.

In an embodiment, the synthesis mixture further comprises at least one of a surfactant, a binder or a plasticizer. In an embodiment, the synthesis mixture further comprises a surfactant. In an embodiment, the surfactant is thermo-decomposable. In an embodiment, the surfactant is selected from the group consisting of poly(ethylene oxide)-poly(propylene oxide)-poly(ethylene oxide) block copolymer (PEO-PPO-PEO), Polysorbate 80, partially-hydrolyzed polyvinyl alcohol (PVA) and combinations thereof. In embodiments, the mass ratio of the surfactant to the carbon precursor is from 1/100 to 100/1 or from 1/10 to 10/1.

In an embodiment, the synthesis mixture further comprises a binder. In embodiments, the binder is water soluble or comprises water soluble moieties. In a further embodiment, the binder is thermo-decomposable. In an embodiment, the binder is selected from the group consisting of poly(vinyl butyral-co-vinyl alcohol-co-vinyl acetate), polyacrylamide, polyvinyl alcohol (PVA), partially-hydrolyzed polyvinyl alcohol (PVA) and combinations thereof. In an embodiment, the mass ratio of inorganic material to binder is from 1/10 to 10/1.

In an embodiment, the synthesis mixture further comprises a plasticizer. In an embodiment, the plasticizer is selected from the group consisting of water, polyethylene glycol, polyol, polyamine or a combination thereof. In embodiments, the mass ratio of the plasticizer to the inorganic material is from 1/10 to 10/1, or from 1/5 to 5/1, or 1/1 to 3/1, In an embodiment, the synthesis mixture comprises polyvinyl alcohol (PVA), functioning as both the surfactant and the binder. In an embodiment, the polyvinyl alcohol is partially hydrolyzed. In an embodiment, the synthesis mixture further comprises 1,3-propanediol (PD), functioning as both the dispersant and the plasticizer. In embodiments, within the synthesis mixture, the mass ratio of colloidal silica to PVA is in the range from 1/10 to 50/1, or from 1/5 to 5/1. In embodiments, within the synthesis mixture, the mass ratio of colloidal silica to PD is from 1/10 and 100/1, 1/5 to 5/1. In an embodiment, other reagents are added into the mixture to improve the properties of intermediate and final products.

In an embodiment, the mixture further comprises one or more additional additives. In embodiments, the additive is a liquid or a solid. Solid additives include, but are not limited to particulate materials and fibrous materials. In an embodiment, fibrous additives include, but are not limited to, carbon fibers and glass fibers. In an embodiment, the additive is selected from the group consisting of an alcohol, a phenolic (e.g. a phenol), an iron compound, a silicon compound other than silica, a titanium compound other than titania, carbon nanotubes, graphene, graphene oxide, carbon nanofibers, a polymer, and a plastic. In an embodiment, the additive is an alcohol. In an embodiment, the additive is n-butanol. In embodiment the weight percentage of the additive within the mixture is less than 50%, less than 10%, from 1% to less than 50%, from 1% to less than 10%, or less than 10%.

In an embodiment, a carbon precursor mixture comprising the carbon precursor material and a first additional component and an aqueous inorganic particulate mixture comprising the inorganic particulate material and water are formed separately and then combined. In an embodiment, the carbon precursor material and the first additional component are both solids and are mechanically milled or ground together to form the carbon precursor mixture. In an embodiment, the carbon precursor material is in particulate form and the mechanical milling or grinding process also reduces the particle size of the precursor material. In an embodiment, the first additional component comprises a water soluble polymer. In a further embodiment, the weight average molecular weight ($M_w$) of the polymer is from 5,000 to 50,000 or from 10,000 to 40,000. In an embodiment the water soluble polymer is polyvinyl alcohol (PVA) or partially hydrolyzed PVA. In an embodiment, the water soluble polymer functions as a binder in the composite film. In a further embodiment, the water soluble polymer performs additional functions in the synthesis mixture, such as acting as a surfactant. In an embodiment, this water soluble polymer is substantially removed from the composite film during the carbonization step such that less than 5 wt % or less than 10 wt % of the binder component remains after carbonization is complete. In embodiments, the mass ratio of the water soluble polymer to the carbon precursor in the synthesis mixture is from 1/100 to 100/1 or from 1/10 to 10/1.

In an embodiment, the aqueous inorganic particulate mixture comprises a second additional component. In an embodiment, the second additional component is an alcohol. In an embodiment, the weight percentage of the second additional component within the mixture is less than 50%, less than 10%, from 1% to less than 50% or from 1% to less than 10%.

In an embodiment, the aqueous inorganic particulate mixture comprising the inorganic particulate material and water further comprises a third additional component selected from polyethylene glycol, polyol, or polyamine. In an embodiment, the third additional component is a polyol. In an embodiment, the polyol is 1,3 propanediol. In embodiments, the mass ratio of the plasticizer to the inorganic material in the synthesis mixture is from 1/10 to 10/1, or from 1/5 to 5/1, or from 1/1 to 3/1.

In a further embodiment, the aqueous inorganic particulate mixture further comprises a stabilizing component for the suspension or slurry. In an embodiment, the stabilizing agent is a cationic stabilizer.

In different embodiments, the synthesis mixture is deposited on the substrate by tape casting, spin casting, dip coating, spray coating, screen printing, roll coating, gravure coating or by other means as known in the art. When tape casting is used, the layer thickness may be adjusted by adjusting the component concentration of the ink or by adjusting the gap between the doctor blade and the substrate. In an embodiment, the thickness of the film is from 0.1 μm to 10 mm. Suitable substrates include, but are not limited to, glass, plastics, metal or a ceramic. In an embodiment, a reinforcing material, such as a grid or fabric, is incorporated into the carbon-based material by depositing the synthesis mixture over the reinforcing material.

In different embodiments, water is removed from the film after deposition through exposure to ambient atmosphere at ambient temperature (e.g., room temperature, 15° C. to 25° C.) for less than 1 hour to more than 2 days. In other embodiments, the cast ink may be dried under a range of humidity or other vapor atmospheres at different temperatures. During the drying step, not all of the water need be removed from the film. In an embodiment, the film after drying but before carbonization is gel-like or plastic in nature. In an embodiment, the film is separated from the substrate after drying and prior to subsequent processing steps.

In an embodiment, the film is heated to produce a composite film comprising carbon and the inorganic particulate material. In an embodiment, the film is carbonized by heating to a temperature of 500° C. to 1500° C. In embodiments, the film is held at this temperature for a time from 0.1 to 48 hours or for about two hours. In an embodiment, the film is preheated prior to exposure to the carbonization temperature. In an embodiment, the temperature of the film is gradually increased to the carbonization temperature during the preheating step. In an embodiment, the film is exposed to a temperature from 500° C. to 1500° C. for 0.1 to 48 hours. In a further embodiment, the film is exposed to a temperature of 100° C. to 500° C. for 0.1 to 48 hours prior to exposure of the film to a temperature from 500° C. to 1500° C. In an embodiment, the temperature to which the film is exposed is increased from room temperature at a ramp rate of 0.1 to 100° C./minute or 1° C./minute to 10° C./minute. In another embodiment, the heating step combines gradual increases in the temperature with one or more hold times at intermediate temperatures (e.g., holding at 400° C. for 0.1-10 hours). The film may be partially constrained during the preheating and/or carbonization steps. In an embodiment, the film is placed between two plates. In an embodiment, the plates are porous. In an embodiment, a plurality of films undergo preheating and/or carbonization at the same time. In an embodiment, a film is placed between two other films during the preheating and/or carbonization steps. In an embodiment, the film is held under pressure during carbonization; in an embodiment, the pressure varies during the carbonization step. In an embodiment, the heat treatment takes place in a non-oxidative atmosphere. In different embodiments, the heat treatment may be conducted in an atmosphere of nitrogen, helium, argon or mixtures thereof. In an embodiment, the heat treatment may be conducted in an oxidative atmosphere (e.g., air) for a certain time. The resulting composite film may be cooled prior to subsequent processing.

In an embodiment, at least a portion of the particulate "template" material is removed from the composite film by dissolving the template material from the composite film. The size and shape of the pores within the films can be adjusted by selecting the particle size and shape of a removable template material. In different embodiments, an acidic or a basic solution is used to dissolve the template material. In different embodiments, the composite film is exposed to the solution for sufficient time to dissolve most of the template, at least 90 vol % of the template, or at least 95 vol % of the template. In an embodiment, the porous film is washed following synthesis. In another embodiment, the porous film is dried following washing and/or dissolution of the template.

In an embodiment, the specific surface area of the porous carbon-based film is 1 $m^2$/g-2000 $m^2$/g or 10 $m^2$/g-1000 $m^2$/g.

In another aspect, the post-synthesis films are loaded with a catalyst. In an embodiment, the films are loaded with catalyst using one or more than one of the methods known in the art, such as sputter-coating or electro-deposition. In an embodiment, a wet impregnation method is used to introduce a catalyst into the film. For example, a chloroplatinic acid solution can be used to introduce platinum into the NCF. In an aspect, the invention provides a supported catalyst comprising a nanoporous carbon-based film of the invention, and metallic nanoparticles including Pt group metal nanoparticles (NPs), Pd NPs, Ir NPs, Ni NPs, Au NPs, or other metals, such as Ni NPs or Co NPs, or a combination thereof. In an embodiment, the supported catalyst can also be a metal oxide e.g., Ir oxide, Ru oxide, Ni oxide, Ti oxide, Ta oxide, Co oxide, Fe oxide etc. or combination of oxides. In an embodiment, the metal oxide is given by the formula $RuO_x$, $IrO_x$, $TiO_x$, $TaO_x$, $CoO_x$, $FeO_x$, where x indicates the amount of oxygen in the composition. In an embodiment, the metallic or metal oxide nanoparticles are attached to the surface of the carbon-based film. In embodiments, the metallic or metal oxide nanoparticles have a size from 1 nm to 100 nm, from 1 nm to 50 nm, from 1 nm to 25 nm, from 2 nm to 10 nm, or from 2 nm to 5 nm. In embodiments, the catalyst loading is from 10 wt % to 50 wt %, from 10 wt % to 40 wt %, from 20 wt % to 50 wt % or from 20 wt % to 40 wt %.

In another aspect, the invention provides modified carbon-based films, including nanoporous carbon-based films, wherein the carbon-based films are modified with a bio-material. In an embodiment, the bio-material is selected from the group consisting of enzymes, proteins, antibodies, bacteria, DNA, RNA, and combinations thereof In another embodiment, the invention provides a supported catalyst comprising a nanoporous carbon film of the invention and an enzyme or other bio-material attached to the surface of the carbon-based film. The bio-material may stick to the surface of the carbon or may be attached through conjugation.

In another aspect, the invention provides modified carbon-based films, such including nanoporous carbon-based films wherein the films are doped with nitrogen, boron, phosphorus, or a combination thereof. The film may be doped in the framework, on the surface, or a combination thereof.

In an embodiment, the post-synthesis films are functionalized by attaching functional groups to the surface. In an embodiment, the functional groups are selected from the group consisting of pentafluorophenyl, aminophenyl, nitrophenyl, phenyl sulfonic acid, and combinations thereof.

In an embodiment, the post-synthesis films are heat treated in an inert atmosphere. In an embodiment, the post-synthesis films are heat treated in a non-inert atmosphere. In an embodiment, the films are heat treated at a temperature up to 3000° C. in an inert atmosphere. In an embodiment, the heat-treated films are further surface modified with different functional groups.

In an embodiment, the porous carbon-based films of the invention are electrically conducting. In an embodiment, the porous carbon-based films of the invention display an electrical conductivity of 0.001-1000 S/cm or from 2 to 10 S/cm. In an embodiment, the porous carbon films of the invention are proton conducting, after surface modification with proton-carrier groups.

In an embodiment, the nanoporous carbon-based films of the invention display capacitive properties. In an embodiment, the total gravimetric capacitance values (double-layer and pseudo-capacitance together) are from 0.1 to 500 F/g. In an embodiment, the ratio of pseudo-capacitance to double-layer capacitance is from 0 to 1. This ratio reflects the functional group density of the carbons, i.e., the higher the ratio, the higher the surface functional group density.

DETAILED DESCRIPTION OF THE INVENTION

Figures 1A, 1B, 1C:
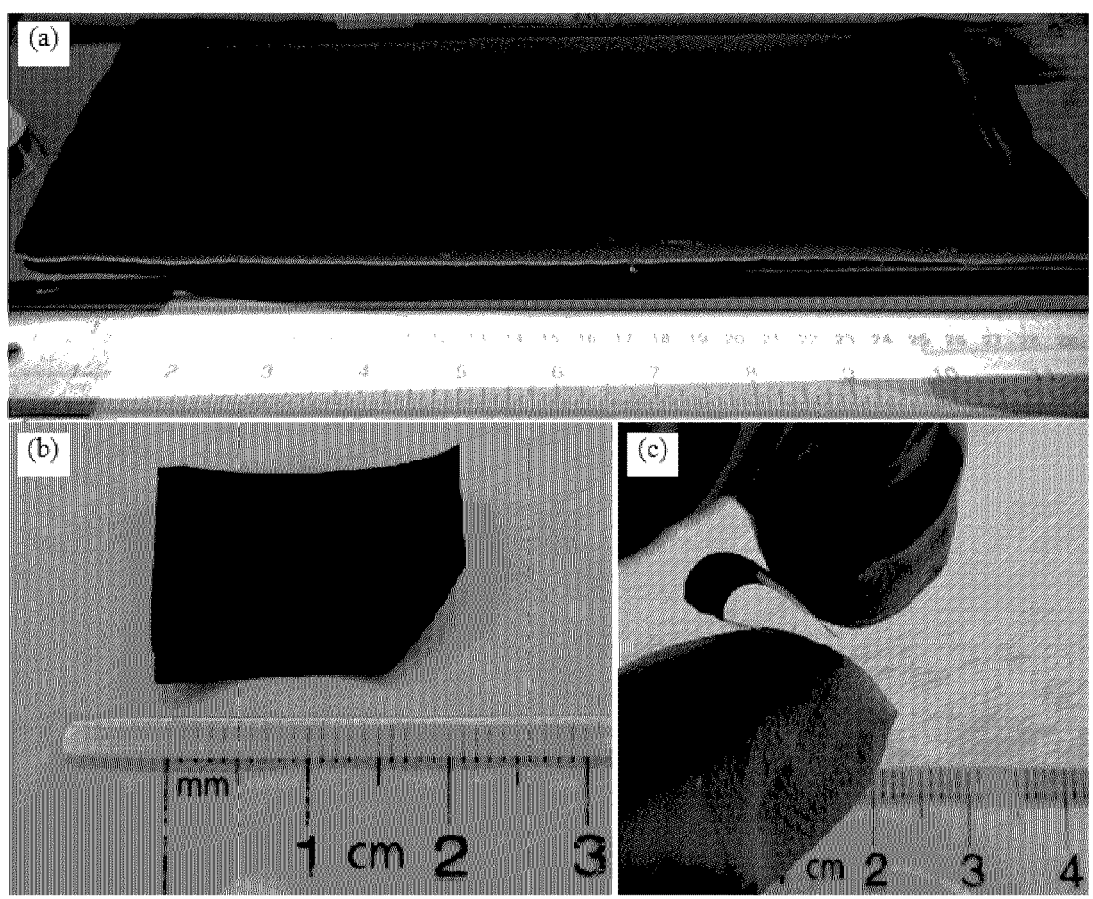
FIGS. 1A, 1B and 1C. 1A) An example of a pristine tape-cast nanoporous carbon film (NCF), formed using mesophase pitch (MP), polyvinyl alcohol (PVA), 1,3-propanediol (PD), and silica on a glass substrate. (1B) A piece of the NCF having a pore size of 80 nm after carbonization and silica removal, with (1C) showing that the film is very flexible.

As used herein, "carbonize" and grammatical variations thereof refer to conversion of a carbon-containing source or carbon precursor to form elemental carbon. A variety of carbon-containing source materials are suitable for the methods of the invention. In an embodiment, the source or precursor material is mesophase carbon pitch. In an embodiment, mesophase pitch is a pitch with a complex mixture of numerous essentially aromatic hydrocarbons containing anisotropic liquid-crystalline particles (carbonaceous mesophase) detectable by optical microscopy and capable of coalescence into the bulk mesophase (PAC, 1995, 67, 473 (*Recommended terminology for the description of carbon as a solid* (*IUPAC Recommendations* 1995)) on page 496, doi: 10.1351/pac199567030473). In an embodiment, a mesophase pitch carbon precursor is selected from the group consisting of naphthalene-based pitch, coal-based pitch, oil-based pitch, and other-source-based pitches. Other suitable sources of carbon include, but are not limited to, carbohydrates (e.g., sucrose), polymers (e.g., phenol formaldehyde resins), polycyclic aromatic hydrocarbons (e.g., anthracene and naphthalene), and other organic compounds.

A range of inorganic materials may be used as templates. In an embodiment, the template material is silica-based. In an embodiment, the silica-based template is colloidal silica. In an embodiment, the colloidal silica is provided in the form of a suspension. Similarly, other silica (or other solid metal oxides) templates, such as hexagonal mesoporous silica (HMS, e.g., SBA-15), may be used to diversify the nanoporous structure of the films. In addition, other types of solid oxides and colloids thereof, such as alumina, titania, etc., are suitable for use as a templating reagent in the synthesis of the films. In an embodiment, the solid oxides can be generated in-situ during the ink preparation, by hydrolyzing or nucleating the precursors of the solid oxides, e.g., tetraethyl orthosilicate (TEOS) to form colloidal silica. In an embodiment, the templates are recycled. For example, the silicates generated from the dissolved templates in aqueous NaOH solutions may be used to synthesize the colloids, and hexafluorosilicic acid ($H_2SiF_6$), if hydrofluoric acid is used as the removing reagent, may also form silica colloids when it is neutralized.

In an embodiment, the synthesis mixture further comprises additional components. Additional components include, but are not limited to carbon, inorganic solids, nanomaterials, surfactants, binders, plasticizers, stabilizers, and other additives. As used herein, a thermo-decomposable or thermally decomposable component, such as a surfactant or binder, decomposes or volatilizes at the temperature used in the carbonization step. In an embodiment, the synthesis mixture further comprises incompletely-hydrolyzed polyvinyl alcohol (PVA), used as both a surfactant and binder. In an embodiment, the extent of hydrolyzation is 80% to 90%. In an embodiment, the incompletely hydrolyzed PVA has a relatively low weight molecular weight (Mw), such as from about 5,000 to about 50,000 or from about 10,000 to about 40,000. In an embodiment, the synthesis mixture further comprises of a polyol, such as 1,3-propanediol (PD), used as the dispersant and plasticizer. In an embodiment, ammonium or other reagents are added into the mixture to stabilize the slurry. In an embodiment, the synthesis further comprises reagents, such as KOH for creating micopores in carbon. In additional embodiments, Fe complexes, or other catalysts, are added to the ink in order to make the nanoporous carbon-based films more graphitic at a lower carbonization temperature. Other additives improve the nanoporous carbon-based film properties, e.g., boron for corrosion resistance.

A variety of substrates are suitable for use in the methods of the invention. In an embodiment, preferred substrates are smooth and/or flat. The substrate may be surface treated before casting the ink. When using a metallic substrate (e.g., Sn and Al), an electrical potential can be applied to the cast ink.

In an embodiment, the drying step produces a gel-like or plastic film comprising templating particles distributed in a matrix comprising the carbon precursor, surfactant, binder, plasticizer, and other additives. The distribution of the templating particles within the matrix need not be uniform. For example, settling of the particles can result in a higher volume fraction of particles near the substrate. In addition, some aggregation of the template particles can occur, especially for smaller template particle sizes (e.g., less than 20 nm). If close packed structures of the template particles form, such as through particle settling and/or aggregation, penetration of the carbon precursor into the close-packed structure can be limited. In an embodiment, distribution of the template particles within the matrix is improved through use of reagents to adjust the pH of the synthesis mixture and/or through use of reagents to improve the suspension of the template particles in the mixture.

In an embodiment, each stage of the nanoporous carbon-based film preparation is controlled to minimize damage due to shrinkage or expansion during the carbonization step. In other embodiments, rapid changes during the heating step may be used to generate unique structures within the films.

In an embodiment, the precursor films are sandwiched between plates during the heating process. An ideal holder for the precursor films applies little friction to the nanoporous carbon-based films, while also being porous so that any volatiles can be removed from the films quickly. In an embodiment, carbon-coated alumina plates are used to sandwich the film.

In an embodiment, carbonaceous regions in the film are interconnected to form a porous structure and a binder is not required to conjoin the carbonaceous regions of the carbonized film. According to the model of close-packing of spheres for the colloid-imprinting method, the carbon wall thickness is linearly dependent on the pore size. The 3-dimensional inter-connectivity of the pores can be sacrificed to increase the wall thickness of small diameter pores by preventing the colloids from close packing. If desired, methods to thicken the carbon walls and also to retain the 3-dimensionally connected pores include, but are not limited to, increasing the MP content of the precursor films and using partially surface-functionalized carbon to serve as spacers, thus lowering the density of the pores in the nanoporous carbon-based films (equivalent to thickening the carbon walls). If desired, methods to thin the carbon walls and also to retain the 3-dimensionally connected pores include, but are not limited to, decreasing the MP content of the precursor films and adding the precursor of templates to decrease the volume among template particles, thus thinning the pore walls of the nanoporous carbon-based films.

As used herein, with respect to the pore structure of a film, "nanoporous" refers to pores having diameters ranging from <1 nm up to about 100 nm. In an embodiment, a nanoporous film comprises nanopores, but may also comprise some larger pores. In another embodiment, the nanoporous film has a narrow pore size distribution. In different embodiments, the synthesis methods, modification, and applications of the nanoporous carbon films, as described in this patent, are also able to be used for carbon films with pores smaller than 2 nm or larger than 100 nm.

In an embodiment, the pores within the films are interconnected 3-dimensionally. In an embodiment, formation of 3-dimensionally interconnected pores is facilitated by sintering of template materials. In an embodiment, the temperatures used during the carbonization step cause sintering of silica colloids during the carbonization step. In another embodiment, additives are used in the slurry preparation to promote the formation of 3-dimensionally interconnected template materials, and hence pores. In an embodiment, tetraethyl orthosilicate (TEOS) or other oxide precursors are used as an additive for this purpose; these components can be used in combination with silica colloids. A variety of methods for measuring pore size are known to the art, including microscopy analysis (such scanning electron microscopy (SEM) and transmission electron microscopy (TEM)). Pore connectivity can be assessed through microscopy and gas adsorption isotherms.

In an embodiment, a basic solution is used to dissolve the template material. Suitable basic solutions include, but are not limited to, NaOH solutions. In an embodiment, an acidic solution is used to dissolve the template material. Suitable acidic solutions include, but are not limited to, HF. In an embodiment, the basic solution is 0.001 M to 18 M NaOH. In an embodiment, the acidic solution is 0.001 wt % to 100 wt % HF. In an embodiment, the dissolution time is from 0.01 hour to 10 days and often about 2 days. The dissolution may be conducted at a temperature greater than ambient or room temperature. In an embodiment, the dissolution temperature is up to the boiling point of the basic or acidic solution. The dissolution may be conducted under an inert atmosphere or non-inert atmosphere, e.g., in air.

Nanoporous carbon-based films can be supported by other materials in order to achieve higher mechanical strength or electrical conductivity. In an embodiment, carbon fiber paper (CFP) is used as a support because of its similar chemical composition, good compatibility, similar thermal extension coefficients, and high-temperature stability (under an inert atmosphere). In an embodiment, the carbonized nanoporous carbon-based film (before or after removing silica) is attached to CFP with PVA (or other binders), followed by pyrolysis of the PVA (or the binder). Other materials (e.g., MP) may be added to the PVA solution (even replacing it) for the purpose of attaching the nanoporous carbon-based films onto a support.

The nanoporous carbon-based films can be loaded with various catalysts, such as Pt nanoparticles and enzymes for organic and biological synthesis. The catalysts can be loaded directly onto the self-supporting nanoporous carbon-based film, or on the supported films. The catalysts can be loaded onto the surfaces of the nanoporous carbon-based film using methods known to the art, such as wet impregnation, sputter-coating, precipitation, electrodeposition, and so on. In an embodiment, the catalysts are distributed within the nanoporous carbon-based films in a graded manner, either through the nanoporous carbon-based film or along its length, or in other patterns.

All references cited herein are hereby incorporated by reference to the extent not inconsistent with the disclosure herewith.

Although the description herein contains many specificities, these should not be construed as limiting the scope of the invention but as merely providing illustrations of some of the presently preferred embodiments of the invention. Thus, the scope of the invention should be determined by the appended claims and their equivalents, rather than by the examples given.

When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods, other than those specifically exemplified can be employed in the practice of the invention without resort to undue experimentation. All art-known functional equivalents, of any such methods, device elements, starting materials, and synthetic methods, are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing,", "composed of", or "characterized by," and is inclusive or open-ended and does not exclude additional, unrecited elements or method steps. As used herein, "consisting of" does not exclude any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general, the terms and phrases used herein have their art-recognized meaning, which can be found by reference to standard texts, journal references and contexts known to those skilled in the art. The preceding definitions are provided to clarify their specific use in the context of the invention.

The invention may be further understood by the following non-limiting examples.

EXAMPLE

1. Introduction

In the work described in this example, a scalable method was developed to prepare self-supporting nanoporous carbon films (NCFs), based on colloid imprinted carbons (CICS) and involving the following steps: 1) casting an aqueous precursor mixture that includes carbon precursor(s), surfactant(s), silica-based structure templates, binder(s), plasticizer(s), and additives, on a substrate, 2) drying the mixture to form a film, 3) heat-treating (carbonizing) the film, and then 4) removing the silica template. Tape-casting is the preferred method to prepare these films, as it is applicable for manufacturing at a large scale [7, 16, 17]. The thickness of the films can be controlled (e.g. from 100 nm to 1 mm) by changing the concentration of the aqueous precursor mixture or adjusting the gap between the doctor blade and the substrate during tape-casting. The pore size of the films in this example was controlled by using silica nanoparticles with different diameters as the template, with the pores ranging from 7 nm to 80 nm. The films can be loaded with catalysts via a wet impregnation method. The synthesized films show very promising properties and are expected to be applicable in a wide variety of fields.

2. Experimental Section 2.1 Slurry Preparation

One procedure used to prepare nanoporous carbon films with a pore size of x nm (x=7, 12, 22, 50, or 80) was as follows. 0.100 g mesophase pitch (MP, AR Grade, Mitsubishi Chemicals, Japan) and 0.200 g n-butanol were mixed in a 20 mL low density polyethylene (LDPE) bottle and then ball-milled (70 rpm, 2 hours) using 32 g of alumina balls, each 4 mm in diameter. 5.00 g of 10 wt % polyvinyl alcohol (PVA, Alfa Aesar, 86-89% hydrolyzed, low molecular weight) in water was then added to the bottle and this mixture was then ball-milled for another 3 h to produce a homogeneous MP/PVA ink.

A colloidal silica suspension (Ludox-HS-40, Ludox-AS-40, NanoSol-5050S, or NanoSol-5080S, in this case with an average colloid size of x nm, x=12, 22, 50, or 80, respectively), containing 0.5 g of silica, was added to 1.0 g of 1,3-propanediol (PD) and water (mass ratio: 1:1) to produce a silica suspension. To obtain a 7 nm sized silica suspension, 1.66 g of Ludox-SM-30 colloidal suspension was dispersed into 5 g of 30% PD/water solution. (Note: All colloids are stabilized with Na cations, except Ludox-AS-40, which is stabilized with ammonia, as shown on their MSDS sheets) The silica suspension was added to the MP/PVA ink and the mixture was ball-milled for 4 h to obtain the MP/PVA/PD/silica ink (or slurry). The ink was degassed under house vacuum for 15 min to remove any trapped bubbles before use.

2.2 Carbon Film Preparation

The slurry was cast on a glass substrate using a casting blade with a 0.010 inch (0.254 mm) gap between the doctor blade and the substrate. After drying overnight, a pristine composite MP/PVA/PD/silica film (FIG. 1A) was obtained. The film was cut into small pieces and placed between two carbon-coated alumina plates. This assembly was inserted into an alumina tubular furnace and carbonized at 900° C. for 2 h in a nitrogen atmosphere, heating at a ramp rate of 0.1-2° C./min. Prior to reaching 900° C., the temperature was held at 400° C. for 2 h. The use of different heating protocols may lead to differences in the properties of the film product. For example, too high a heating rate may result in a weak carbon film. After cooling, the carbonized films were soaked in 3 M NaOH at 80° C. for 2 days to remove the silica template. Following this, the films were washed with deionized water a few times to a neutral state and then soaked in diluted HCl for one day to remove any $Na^+$ ions still attached to the carbon surface. After washing with deionized water several times, the films were placed in an oven for drying in air at 80° C. overnight. The resulting self-supporting nanoporous films (FIG. 1B) were stored in conductive containers, e.g., aluminum covered Petri dishes, to avoid electrostatic effects. These nanoporous carbon films were labelled as NCF-x, with "x" corresponding to the template silica particle size of x nm.

2.3 Catalyst Loading

The carbon films can be loaded with Pt using a wet impregnation procedure [1], with an example as follows. 0.0060 g of $H_2PtCl_6 \cdot 6H_2O$ was dissolved in 0.0755 g acetone in a small vial. The chloroplatinic acid solution was added to 0.0041 g of NCF-22 (ca. 7 $cm^2$ in geometric area). After evaporation of the acetone in room conditions, the composite was placed in a tubular furnace and heated to 300° C. under a $H_2$ atmosphere over a period of 2 h. The sample was maintained at this temperature for 2 h under $N_2$ and was then cooled to room temperature. The obtained sample was named as Pt/NCF-22, with a Pt content of ~32 wt. %.

3. Characterization of NCFs

FIG. 1A shows an optical image of the pristine MP/PVA/PD/silica composite film on a glass substrate, cast using a doctor blade assembly. Clearly, a large area film can be readily prepared through the tape-casting method. An example of this type of synthesized NCF is shown in FIG. 1B. FIG. 1C also shows that the NCF film is very flexible. After releasing it, the bent film in FIG. 1C flattens out again, thus showing very good elasticity. The flexibility of these self-supporting carbon films is particularly advantageous for some applications, such as in rollable batteries.

Figure 2A:
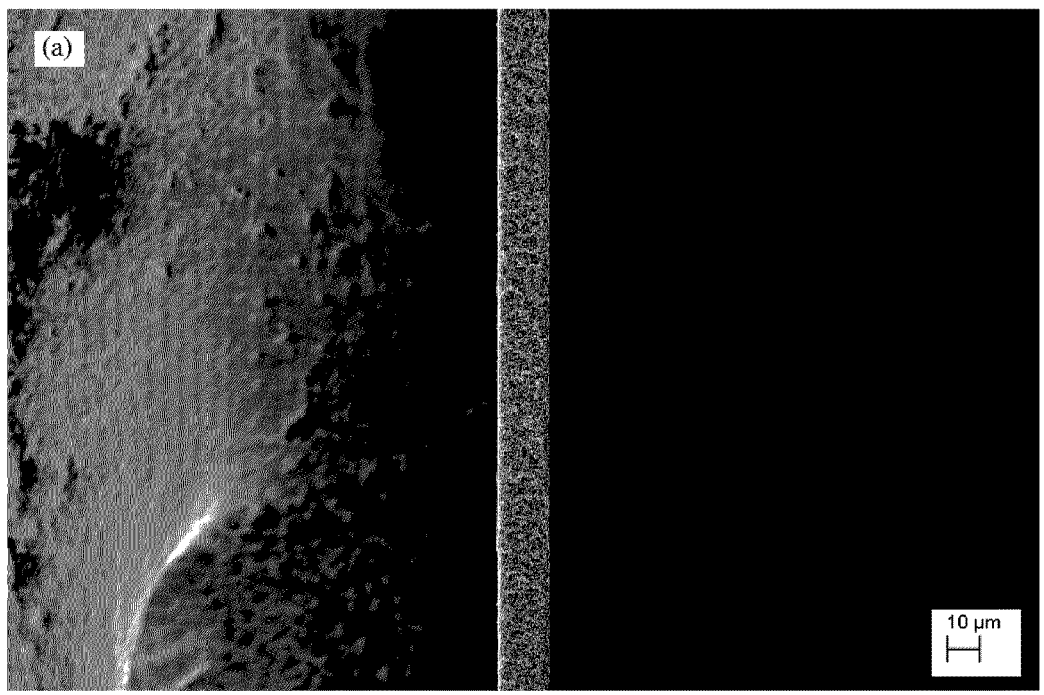
FIGS. 2A-2B. Field-emission scanning electron microscopy (FE-SEM) images of the cross-section of NCF-50 tapes (with nominal pore size of 50 nm) at (2A) low (1000 times) and (2B) high (500,000 times) magnifications.
Figure 2B:
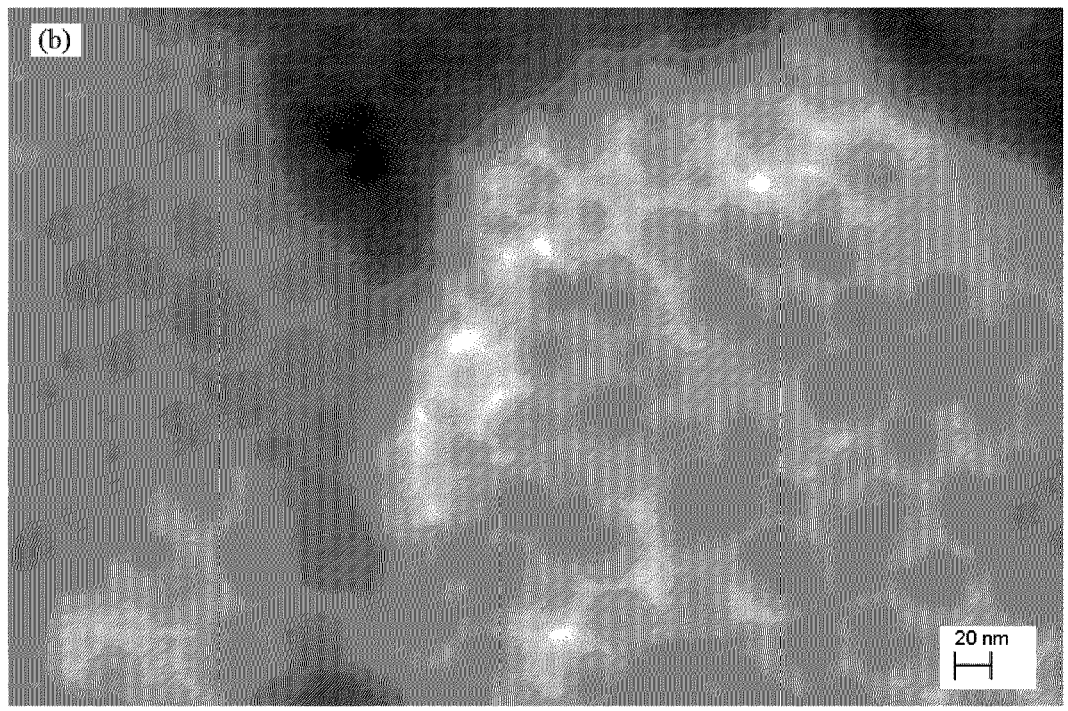
Figure 3A:
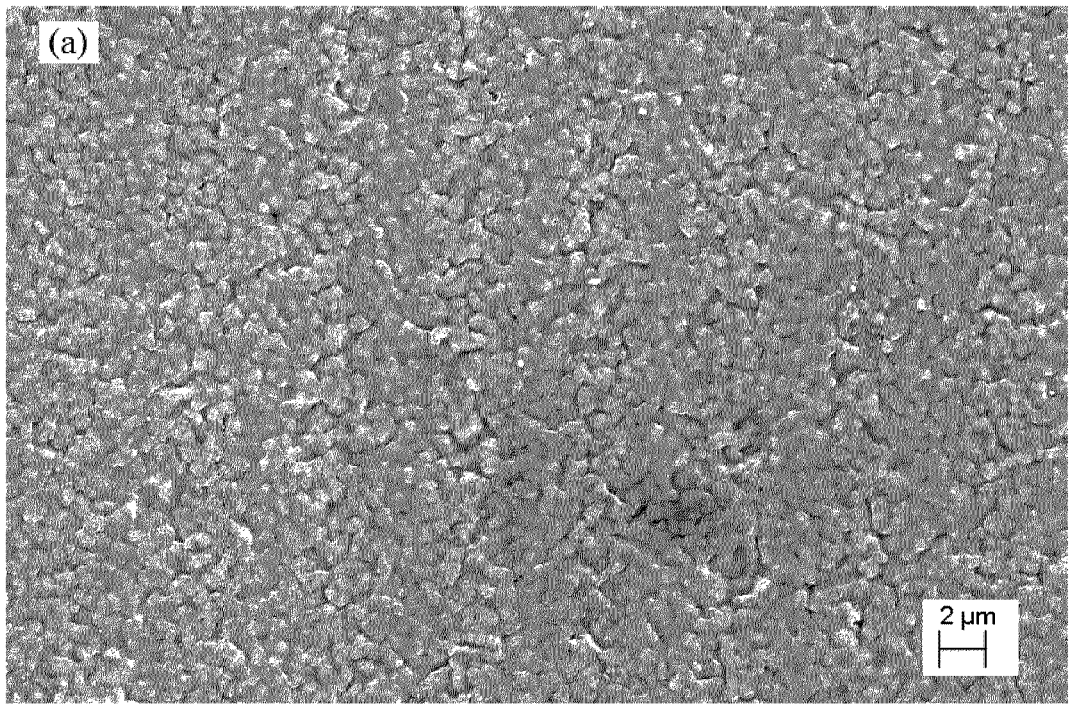
FIGS. 3A-3B. FE-SEM images of the surface of NCF-50 tapes at (a) low (5000 times) and (b) high (100,000 times) magnifications.
Figure 3B:
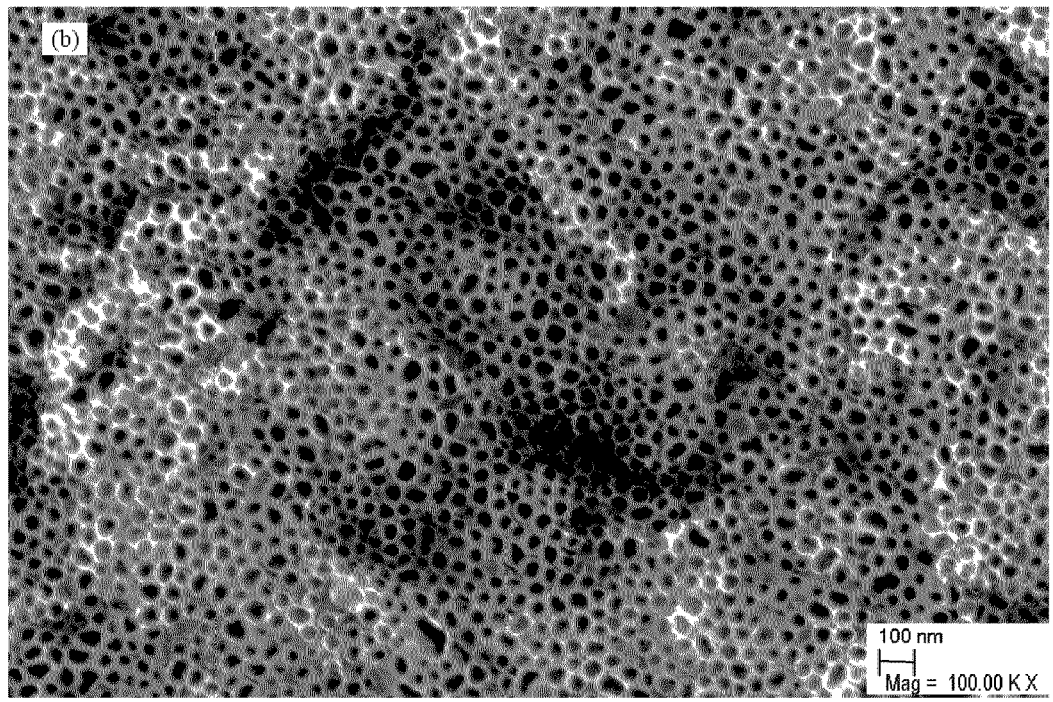
Figure 4:
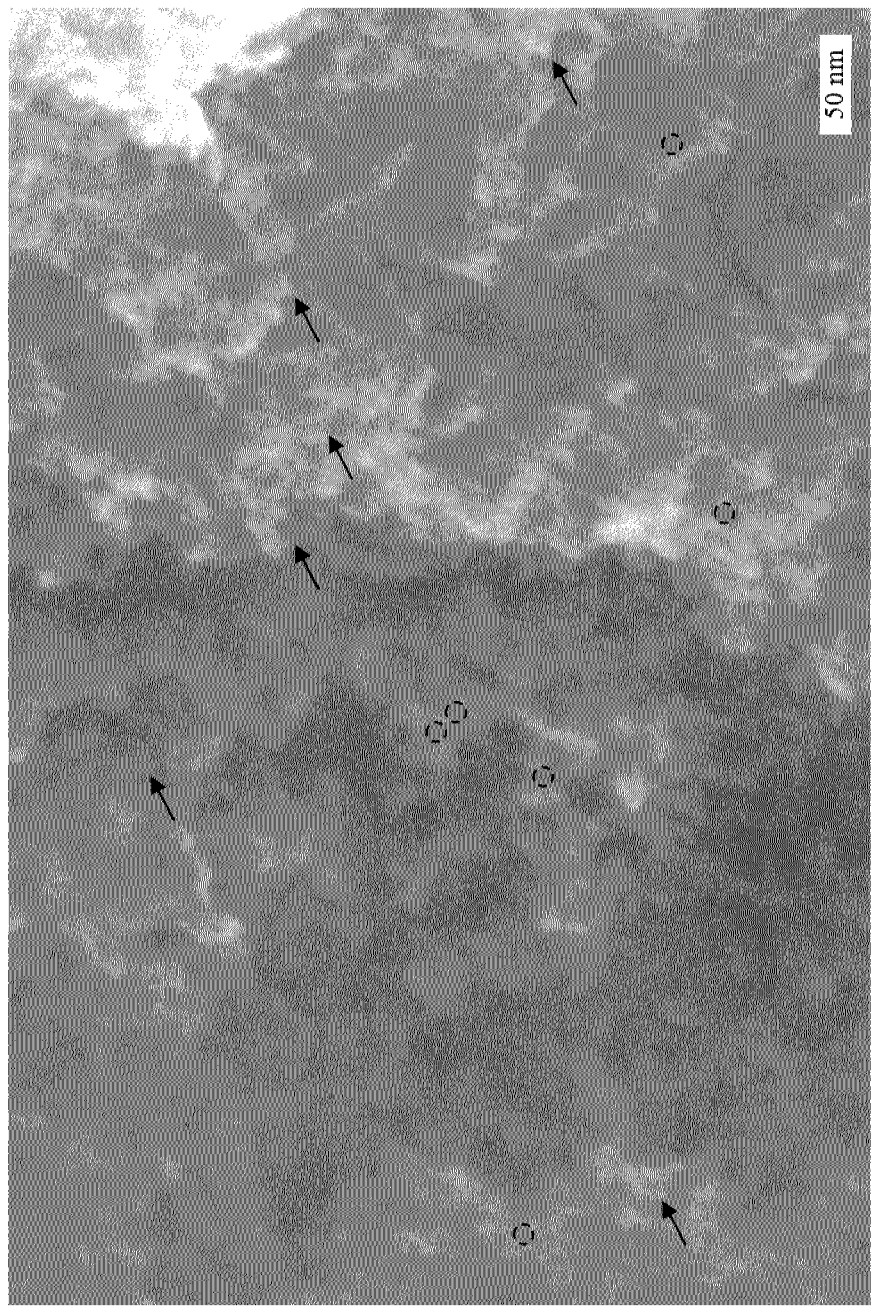
FIG. 4. FE-SEM image of the porous walls of NCF-7 (with nominal pore size of 7 nm) at a magnification of 460,000 times. Individual 7 nm pores are circled in a dashed red line and some pore walls are pointed at by red arrows.

The prepared NCFs were characterized with field-emission scanning electron microscopy (FE-SEM), prior to which the sample surfaces were attached onto conductive carbon tapes. Some examples of the SEM images are shown in FIGS. 2-4. FIGS. 2A-2B-show the cross-section of NCF-50. As a typical example of the NCF tapes, the as-synthesized NCF-50 has a thickness of ca. 15 μm (FIG. 2A) and well-controlled pores of ca. 50 nm within the films (FIG. 2B). The surface of NCF-50 is shown in FIGS. 3A-3B. 3, demonstrating that the film has a very uniform surface (FIG. 3A) and a high density of open nanopores (FIG. 3B). The pores shown in FIG. 3B do not appear perfectly circular because of the direction of imaging. FIG. 4 shows the size of the nanopores of NCF-7, as an example of the prepared carbon films with the smallest colloids used in this example. These results prove the well-controlled thickness and nanoporous structures of the carbon film of this invention.

The electrical conductivity of the as-synthesized NCFs was measured with the van de Pauw method, showing that the NCFs have a conductivity of 2-10 S/cm in this example.

Figure 5:
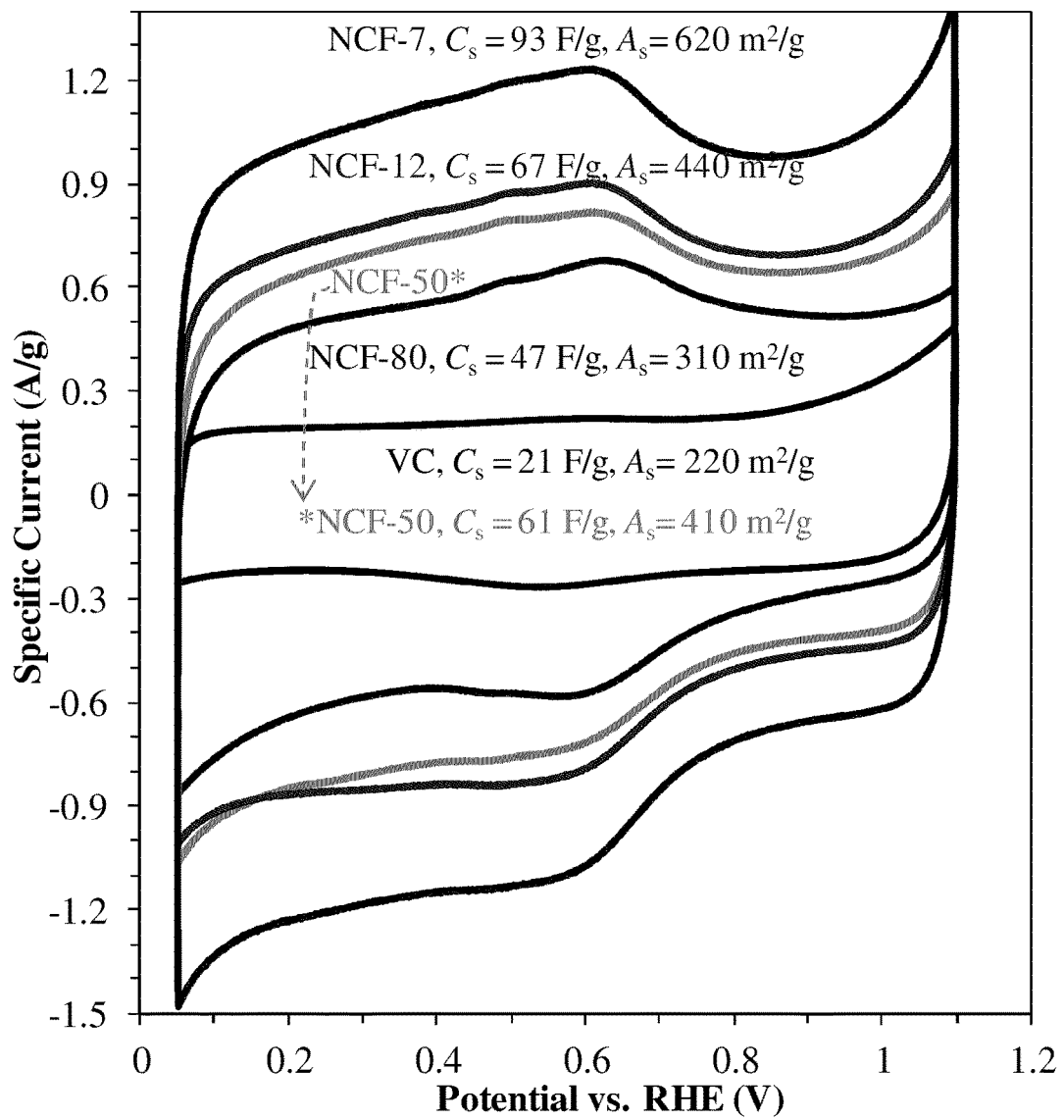
FIG. 5. Cyclic voltammogrametric (CV) responses of NCFs with variable sized pores (the number following NCF is the pore size in nanometers), as well as Vulcan carbon (VC) particles bound with Nafion, in $N_2$-saturated, room temperature, 0.5 M $H_2SO_4$, at a scan rate of 10 mV/s. The gravimetric capacitance ($C_s$) was obtained by integrating the full CV charge passed between 0.05 and 1.1 V (vs. RHE), and dividing the charge by the potential difference of 1.05 V. The estimated specific surface area ($A_s$) was obtained by dividing the total measured capacitance ($C_s$) by the value of 0.15 C per real $m^2$, reported for ordered mesoporous carbons [15], while the surface area of VC was calculated from the nitrogen adsorption/desorption data using BET analysis [2].

The NCFs were also characterized in this example with cyclic voltammetry (CV), carried out in a three-electrode cell containing 0.5 M $H_2SO_4$, a platinized Pt mesh as the counter electrode, and a reversible hydrogen (RHE) reference electrode. The CV results are shown in FIG. 5, indicating that the NCFs have a higher capacitance and thus a higher surface area as compared to the commercial carbon black (VC). It was also found that, a NCF with a smaller pore size has a higher capacitance and thus a higher surface area [15], as expected. In FIG. 5, the template size in nm is indicated by the number following NCF.

Figure 6:
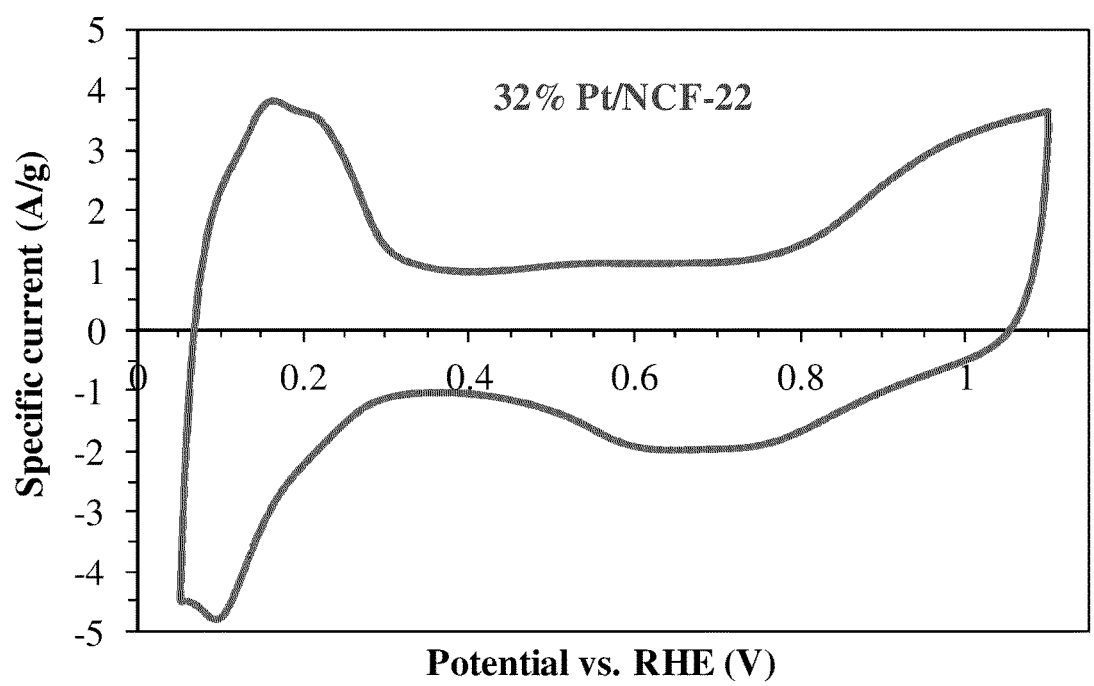
FIG. 6. CV response (10 mV/s) of a 32 wt. % Pt-loaded NCF with 22 nm pores in $N_2$-saturated 0.5 M $H_2SO_4$ at room temperature.

The CV of Pt/NCF-22 (FIG. 6) suggests a very good distribution of Pt nanoparticles (estimated particle size of ~4.7 nm) on the nanoporous surface of the carbon films, based on our previous work [18].

4. Other Properties and Potential Applications of the NCFs

These materials are also useful for nano-filtration [19], for example. Combined with the structural pores (dia.>100 nm), the 3-D inter-connected pores provide many pathways for the mass transfer of fluids passing through the films and thus lower the possibility of blockage of fluid channels, which is very important for applications involving multiple phase transfer.

The edges of the NCFs are typically sealed before using them in a filter assembly. In a filter assembly, glass/Nylon porous frits can support the films. Even so, it can be desirable to support the films by carbon fiber paper (CFP) for use in filtration. To seal the edges of the NCFs, a sealing material that is dense, stiff, but not brittle, tolerant to various chemicals (as many as possible) and electrical potentials, is desired. Desirable precursors are highly viscous liquids exhibiting low shrinkage at the processing stage. Some suitable sealing materials are pitch-derived carbon, phenol-formaldehyde resins (PF), urea-formaldehyde resins (UF), polypropylene (PP), polybutadiene acrylonitrile (PBAN) copolymer, polybutadiene, polystyrene, acrylonitrile butadiene styrene (ABS) copolymer, Nylon, Teflon®, etc.

In an embodiment, the filters of the invention are suitable for electro-filtration. For example, nanosized silica colloids tend to agglomerate on a filter paper/membrane and block its pores, significantly slowing down the filtration rate. An applied electric field can prevent this agglomeration by repelling the charged colloids from the filter. Conductive filters may also discharge electrostatic particulates, decreasing harmful electrostatic effects.

Mesophase pitch (MP), which is a by-product of the petroleum industry, is preferred as the carbon precursor for this work, because MP has a higher percentage conversion to carbon (ca. 75%) than most other carbon precursors, and as the formed carbon is denser and more crystalline, as shown for the colloid-imprinted carbon (CIC) powders in our previous work [1, 2]. This results in dense pore walls and thus a high strength and conductivity of the NCFs. We have also shown (FIGS. 1A, 1B, 1C) that the NCFs have very good self-supporting characteristics and good elasticity, as well as good electrical conductivity (2-10 S/cm). These properties make the NCFs a very promising electrode material for electrochemical applications, such as in supercapacitors and fuel cells.

Another important advantage of using MP as the precursor is that the synthesized NCFs are expected to have a high specific density of active sites on their surfaces, reflected partially by their much larger pseudo-capacitance peaks than VC in FIG. 5. At the imprinting stage, the MP particles, which include polycyclic aromatic hydrocarbons, deposit in an ordered, close packed fashion on the silica particle surfaces, according to the literature [20]. After carbonization and removal of the silica template, the packed planar graphene sheets form the internal walls of the carbon pores and leave the sheet edges, which are more active than the planar surfaces, exposed [20]. The high concentration of active sites on the carbon wall surface enhances the distribution of catalytic nanoparticles [1, 2] and facilitates the chemical functionalization of the nanopore wall surfaces. These benefits have been shown in our work with CIC powders [1, 2]. Another advantage of the presence of densely packed graphene sheets in the pore walls is that they provide easy access for lithium ions to intercalate into the space between graphene sheets, which is important for rapid charging/discharging of lithium batteries.

As discussed above, the surface of the NCFs can be readily functionalized because of its high density of active sites, further broadening their range of applications. For example, after functionalization with sulfonic acid groups, the NCFs can be used as catalysts in organic synthesis. As well, surface-modified carbon films can be applied in chromatography as a stationary phase to separate species or used as adsorbents for water cleaning or other purposes. The carbon surface can also be grafted with chiral or bio-active groups. In combination with the controllable pore size of the films, the NCFs are useful in pharmaceutical applications as well. After surface-grafting with basic/acidic groups, the NCFs can also be used as catalyst layers in low-temperature fuel cells, after loading with catalyst nanoparticles (e.g., Pt), where the basic or acidic groups on the NCF surfaces function as immobile ionic conductors.

The pore size, surface area and pore volume of the NCFs are controllably modified by using different templates, carbon precursors, additives, or by changing the preparation parameters (e.g., heating rates). For instance, high surface areas are easily achieved by using small-size silica templates, as suggested by FIG. 5. They are also obtained by selecting carbon precursors that can generate a large surface area, such as sucrose, or by adding KOH or other reagents that promote the formation of micropores in carbon. In embodiments, the NCFs are doped with other elements to modify their properties. For example, the carbon films are doped with boron by using boric acid as an additive during ball-milling to increase their resistance to corrosion in oxidizing conditions, or nitrogen to serve in fuel cell cathodes.

As in the example demonstrated above, the carbon films can be loaded with catalysts for use as novel, non-ink based catalyst layers (in the form of preformed membranes) in fuel cells or other applications. The catalysts include Pt, Pd, and other catalytic elements/compounds, or their composites, and are in the form of nanoparticles or nanometer thick layers. The catalysts can be loaded onto the pore surfaces of carbon films via impregnation, sputter-coating, precipitation, electro-deposition, or other catalyst loading methods.

The three-dimensionally open connected pores of the NCFs maximize the utilization of their high surface areas and the active surfaces of the loaded catalysts, by facilitating the mass transport of any involved reagents, no matter if liquid or gases. The high electrical conductivity of the NCFs is believed to enhance the current flowing to/from the supported catalysts. As mentioned earlier, the surface of the NCFs can also be readily functionalized, which should stabilize the loaded catalyst particles on the carbon surfaces, increasing their durability and performance.

The robust porous structure of the NCFs facilitates the manufacturing of the catalysts. A catalyst-loaded NCF can be easily applied in the products. For example, Pt-loaded NCFs can be used as catalyst layers in PEMFCs by adding some Nafion solution and then pressing onto a Nafion® membrane to form a catalyst coated membrane (CCM). The NCFs can also be enforced with carbon fiber paper (CFP) first and then loaded with Pt nanoparticles. These CFP-enforced NCF composites, with/without catalyst loading, can be directly used in many applications without using other mechanical supports. They can be used in organic synthesis, electrolysis, capacitors, batteries, fuel cells, sensors, solar cells, and other applied areas where high surface area catalysts are required.

5. Application of NCFs in Polymer Electrolyte Fuel Cells 5.1 Electrolyte Membrane Self-supporting Pt-loaded NCF catalyst layers (or a combination of the catalyst layer and gas diffusion layer) make it possible to minimize the thickness of the electrolyte membrane separator in polymer electrolyte fuel cells (PEFCs), e.g., down to ca. 1 μm from the current 50 or 25 μm, retaining the effective separation of reactants at the same time. Here, the catalyst layer (CL) and the combined supporting gas distribution layer provide the needed mechanical strength of the cell, and keep the electrolyte separator in place and prevent it from deforming. As a result, the mechanical strength of the polymer electrolyte membrane (PEM) becomes less important than is the case in current PEFC designs. This decrease in the separator thickness thus significantly lowers the ohmic resistance of the cell, in turn increasing the energy conversion efficiency. This also diversifies the kinds of electrolyte separators that can be used, from commercially available Nafion to other proton-conducting materials, e.g., metal organic frameworks and solid metal oxides. However, too thin a separating layer may allow cross-over of the reactants. Thus, a modified electrolyte layer is used to minimize the diffusion of $H_2$, $O_2$, or methanol through it. The already known methods to enforce Nafion® membranes with stiffer materials, such as silica or functionalized carbon nanotubes, may be used for this purpose. It is desirable for the membrane to have self-healing properties, i.e., automatically blocking any post-production pinholes. In an embodiment, during the preparation of a PEFC, the electrolyte sol/gel is cast onto two self-supporting NCF-based catalyst layers, then pressing them face-to-face to form the membrane electrode assembly (MEA), which significantly simplifies the preparation of the cells.

5.2 Electrolyte within Catalyst Layer

Conventionally, protonic ionomers, e.g., Nafion®, are used as a binder and protonic conductor in the catalyst layer (CL) of a PEFC. However, it has been found that Nafion can re-orient on carbon or Pt surfaces to form a super-hydrophobic surface, which is unexpected, as Nafion is expected to be a proton conductor and water is essential for proton conductivity. The long hydrophobic backbone of Nafion hinders the movement of the sulfonic acid side-chains and thus decreases the proton conductivity, particularly at lower operating temperatures. By using a NCF-based catalyst layer, a binder will no longer be needed, and thus different electrolytes can be used to improve the mass transport of protons and reactants through the catalyst layers, replacing Nafion in current CL designs.

Within the CLs made of NCFs, an ideal electrolyte possesses the following characteristics: transfer protons from the electrolyte membrane into the catalyst layer, onto the catalyst surfaces, or in the opposite direction, with high efficiency; reach all of the catalyst sites, allowing full proton conductance through the catalyst layers; facilitate diffusion of reactant molecules ($H_2$, $O_2$, methanol, formic acid, etc.)

and products (water, $CO_2$, etc.); allow effective proton transfer over a wide range of humidity and temperature. Stability of the electrolyte within the catalyst layer is also important, with no diffusion into the gas diffusion layer. For these reasons, it is desirable to bond the electrolyte onto the surface of NCFs, as reported for other carbon surfaces [21], which is also expected to increase the carbon corrosion resistance. Similar to the structure above, desirable electrolytic groups include $—(CF_2)_n—O—SO_3H$, where n=4-10, and tetrafluorophenyl sulfonic acid (Scheme 1), where sulfonic acid may be replaced by phosphonic acid. These electrolyte groups can be covalently bonded onto the pore surface of the NCFs to promote proton conductivity and corrosion resistance in PEFCs.

Scheme 1. Molecular structures of surface functional groups.

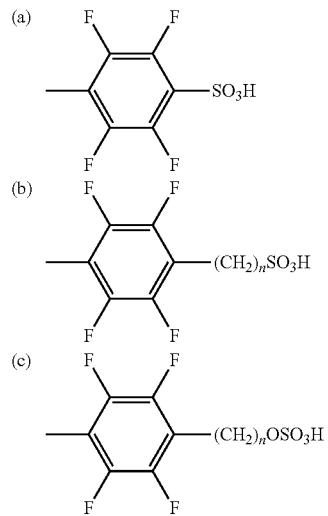

REFERENCES

[1] Banham D, Feng F, Furstenhaupt T, Pei K, Ye S, Birss V. Effect of Pt-loaded carbon support nanostructure on oxygen reduction catalysis. J Power Sources 2011; 196(13): 5438-45.

[2] Pei K, Banham D, Feng F, Fuerstenhaupt T, Ye S, Birss V. Oxygen reduction activity dependence on the mesoporous structure of imprinted carbon supports. Electrochem Commun 2010; 12(11):1666-9.

[3] Kimijima Ki, Hayashi A, Yagi I. Preparation of a self-standing mesoporous carbon membrane with perpendicularly-ordered pore structures. Chemical Communications 2008(44):5809-11.

[4] Liang C D, Hong K L, Guiochon G A, Mays J W, Dai S. Synthesis of a large-scale highly ordered porous carbon film by self-assembly of block copolymers. Angewandte Chemie-International Edition 2004; 43(43):5785-9.

[5] Labiano A, Dai M, Young W-S, Stein G E, Cavicchi K A, Epps T H, III, et al. Impact of Homopolymer Pore Expander on the Morphology of Mesoporous Carbon Films Using Organic-Organic Self-Assembly. Journal of Physical Chemistry C 2012; 116(10):6038-46.

[6] Tanaka S, Katayama Y, Tate M P, Hillhouse H W, Miyake Y. Fabrication of continuous mesoporous carbon films with face-centered orthorhombic symmetry through a soft templating pathway. Journal of Materials Chemistry 2007; 17(34):3639-45.

[7] Korkut S, Roy-Mayhew J D, Dabbs D M, Milius D L, Aksay I A. High Surface Area Tapes Produced with Functionalized Graphene. Acs Nano 2011; 5(6):5214-22.

[8] Mahurin S M, Lee J S, Wang X, Dai S. Ammonia-activated mesoporous carbon membranes for gas separations. Journal of Membrane Science 2011; 368(1-2):41-7.

[9] Song L, Feng D, Fredin N J, Yager K G, Jones R L, Wu Q, et al. Challenges in Fabrication of Mesoporous Carbon Films with Ordered Cylindrical Pores via Phenolic Oligomer Self-Assembly with Triblock Copolymers. Acs Nano 2009; 4(1):189-98.

[10] Chmiola J, Largeot C, Taberna P-L, Simon P, Gogotsi Y. Monolithic Carbide-Derived Carbon Films for Micro-Supercapacitors. Science 2010; 328(5977):480-3.

[11] Moriguchi I, Nakahara F, Furukawa H, Yamada H, Kudo T. Colloidal crystal-templated porous carbon as a high performance electrical double-layer capacitor material. Electrochemical and Solid State Letters 2004; 7(8): A221-A3.

[12] Ye X, Qi L. Two-dimensionally patterned nanostructures based on monolayer colloidal crystals: Controllable fabrication, assembly, and applications. Nano Today 2011; 6(6):608-31.

[13] Wang Q, Moriyama H. Carbon Nanotube-Based Thin Films: Synthesis and Properties: InTech; 2011.

[14] Siegal M P, Overmyer D L, Kottenstette R J, Tallant D R, Yelton W G. Nanoporous-carbon films for microsensor preconcentrators. Applied Physics Letters 2002; 80(21): 3940-2.

[15] Banham D, Feng F, Burt J, Alsrayheen E, Birss V. Bimodal, templated mesoporous carbons for capacitor applications. Carbon 2010; 48(4):1056-63.

[16] Chicharro M, Bermejo E, Moreno M, Sanchez A, Zapardiel A, Rubio-Marcos F, et al. Tape casting of graphite material: A new electrochemical sensor. Electroanalysis 2006; 18(16):1614-9.

[17] Hu X B, Zhong S, Zhao B Y, Hu K A. Processing of an aqueous tape casting of mesocarbon microbeads for high-performance carbonaceous laminations. Carbon 2003; 41(12):2285-93.

[18] Banham D, Feng F, Pei K, Ye S, Birss V. Effect of carbon support nanostructure on the oxygen reduction activity of Pt/C catalysts. J Mater Chem A 2013; 1(8): 2812-20.

[19] Hilal N, Al-Zoubi H, Darwish N A, Mohamma A W, Abu Arabi M. A comprehensive review of nanofiltration membranes: Treatment, pretreatment, modelling, and atomic force microscopy. Desalination 2004; 170(3):281-308.

[20] Zhi L J, Wu J S, Li J X, Kolb U, Mullen K. Carbonization of disclike molecules in porous alumina membranes: Toward carbon nanotubes with controlled graphene-layer orientation. Angewandte Chemie-International Edition 2005; 44(14):2120-3.

[21] Salguero T T, Sherman E, Liu P, inventors; Google Patents, assignee. Chemically modified catalyzed support particles for electrochemical cells. 2011.

We claim:
1. A method for synthesis of a porous carbon-based film, the method comprising the steps of:
   a) forming a mixture comprising particles of an inorganic material, a carbon precursor material, at least one surfactant, at least one binder and water;
   b) forming a layer of the mixture on a substrate;
   c) removing water from the layer to form a film;
   d) removing the film from the substrate;

19 e) heat treating the film for a time sufficient to decompose the at least one surfactant and at least one binder and convert the carbon precursor in the film to carbon, thereby forming a composite film comprising carbon and the particles of inorganic material; and f) removing the particles of inorganic material from the composite film, thereby forming a porous carbon-based film.

2. A method for synthesis of a porous carbon-based film, the method comprising the steps of:
   a) forming a mixture comprising particles of an inorganic material, a carbon precursor material, and water;
   b) forming a layer of the mixture on a substrate;
   c) removing water from the layer to form a film;
   d) removing the film from the substrate;
   e) heat treating the film for a time sufficient to convert the carbon precursor in the film to carbon, thereby forming a composite film comprising carbon and the particles of inorganic material; and
   f) removing the particles of inorganic material from the composite film, thereby forming a porous carbon-based film,
   wherein:
      i) the porous carbon film is self-supporting;
      ii) the porous carbon film is a nanoporous carbon film;
      iii) the inorganic material is a metal oxide;
      iv) the inorganic material is colloidal silica;
      v) the particles of inorganic material are spherical in shape;
      vi) the average size of the particles of the inorganic material is 1 nm to 10 μm;
      vii) the mass ratio of the carbon precursor to the inorganic material is in the range from 1/50 to 5/1;
      viii) in step e, the film is exposed to a temperature from 500° C. to 1500° C. for 0.1 to 48 hours;
      ix) in step e, the film is heated from room temperature to a temperature from 500° C. to 1500° C. at a rate of 0.1° C./min to 100° C./min;
      x) in step e, the film is exposed to a temperature of 100° C. to 500° C. for 0.1 to 48 hours prior to exposure of the film to a temperature from 500° C. to 1500° C.;
      xi) during step e, the film is placed between two plates;
      xii) during step e, the film is placed between two other films;
      xiii) during step e, the film is held under a pressure; or
      xiv) during step e, the film is held under a pressure wherein the pressure varies.

3. The method of claim 1, wherein the carbon precursor is a carbon-generating material selected from the group consisting of pitch, carbohydrate, alcohol, polymer, oligomer, polycyclic aromatic hydrocarbons, and combinations thereof.

4. The method of claim 3, wherein the carbon precursor is a mesophase pitch.

5. The method of claim 1, wherein
the mass ratio of the surfactant to the carbon precursor is from 1/100 to 100/1.

6. A method for synthesis of a porous carbon-based film, the method comprising the steps of:
   a) forming a mixture comprising particles of an inorganic material, a carbon precursor material, at least one binder, and water;
   b) forming a layer of the mixture on a substrate;
   c) removing water from the layer to form a film;
   d) removing the film from the substrate;

20 e) heat treating the film for a time sufficient to convert the carbon precursor in the film to carbon, thereby forming a composite film comprising carbon and the particles of inorganic material; and
   f) removing the particles of inorganic material from the composite film, thereby forming a porous carbon-based film,
   wherein:
      i) the binder is water-soluble;
      ii) the binder is water-soluble and thermo-decomposable;
      iii) the binder is selected from the group consisting of poly(vinyl butyral-co-vinyl alcohol-co-vinyl acetate), polyacrylamide, polyvinyl alcohol (PVA), and combinations thereof; or
      iv) the mass ratio of inorganic material to binder is from 1/10 to 10/1.

7. The method of claim 1, wherein the mixture further comprises at least one plasticizer and/or one or more additives selected from the group consisting of an alcohol, a phenolic, an iron compound, a silicon compound other than silica, a titanium compound other than titania, carbon nanotubes, graphene, graphene oxide, carbon nanofibers, a polymer, and a plastic.

8. A method for synthesis of a porous carbon-based film, the method comprising the steps of:
   a) forming a mixture comprising particles of an inorganic material, a carbon precursor material and water;
   b) forming a layer of the mixture on a substrate;
   c) removing water from the layer to form a film;
   d) removing the film from the substrate;
   e) heat treating the film for a time sufficient to convert the carbon precursor in the film to carbon, thereby forming a composite film comprising carbon and the particles of inorganic material; and
   f) removing the particles of inorganic material from the composite film, thereby forming a porous carbon-based film,
   wherein the mixture further comprises at least one plasticizer and/or one or more additives selected from the group consisting of an alcohol, a phenolic, an iron compound, a silicon compound other than silica, a titanium compound other than titania, carbon nanotubes, graphene, graphene oxide, carbon nanofibers, a polymer, and a plastic; and
   wherein:
      i) the mixture further comprises a plasticizer selected from the group consisting of water, polyethylene glycol, polyol, polyamine and a combination thereof;
      ii) the mixture comprises the plasticizer 1,3-propanediol;
      iii) the mixture comprises a plasticizer and the mass ratio of the plasticizer to the inorganic material is from 1/10 to 10/1;
      iv) the mixture comprises an additive which is n-butanol; or
      v) the mixture comprises an additive and the weight percentage of the additive within the mixture is less than 50%.

9. The method of claim 1, wherein the water content of the mixture is from 1% to 99% in weight.

10. The method of claim 2, wherein the mixture formed in step a further comprises at least one surfactant, and at least one binder, and the heat treating of step e) is conducted for a time sufficient to decompose the at least one surfactant and at least one binder and convert the carbon precursor in the film to carbon.

11. The method of claim 10, wherein the mass ratio of the surfactant to the carbon precursor is from 1/100 to 100/1 and the mass ratio of inorganic material to binder is from 1/10 to 10/1.

12. The method of claim 10, wherein the carbon precursor is a mesophase pitch.

13. The method of claim 11, wherein the mass ratio of the surfactant to the carbon precursor is from 1/100 to 100/1 and the mass ratio of inorganic material to binder is from 1/10 to 10/1.

14. The method of claim 13, wherein the surfactant is selected from the group consisting of poly(ethylene oxide)-poly(propylene oxide)-poly(ethylene oxide) block copolymer (PEO-PPO-PEO), Polysorbate 80, partially-hydrolyzed polyvinyl alcohol (PVA), and combinations thereof.

15. The method of claim 13, wherein the binder is selected from the group consisting of poly(vinyl butyral-co-vinyl alcohol-co-vinyl acetate), polyacrylamide, polyvinyl alcohol (PVA), and combinations thereof.

16. The method of claim 13, wherein the mixture further comprises at least one plasticizer and/or one or more additive selected from the group consisting of an alcohol, a phenolic, an iron compound, a silicon compound other than silica, a titanium compound other than titania, carbon nanotubes, graphene, graphene oxide, carbon nanofibers, a polymer, and a plastic.

17. The method of claim 10, wherein the inorganic material is colloidal silica.

18. The method of claim 17, wherein the average size of the particles of colloidal silica is 1 nm to 10 μm.

19. The method of claim 10, wherein in step e, the film is exposed to a temperature of 100° C. to 500° C. for 0.1 to 48 hours prior to exposure of the film to a temperature from 500° C. to 1500° C., the carbon precursor is a mesophase pitch and the at least one surfactant and at least on binder are thermally decomposable.

20. The method of claim 19, wherein the inorganic material is colloidal silica.

21. The method of claim 2, wherein the carbon precursor is a carbon-generating material selected from the group consisting of pitch, carbohydrate, alcohol, polymer, oligomer, polycyclic aromatic hydrocarbons, and combinations thereof.

* * * * *

UNITED STATES PATENT AND TRADEMARK OFFICE
CERTIFICATE OF CORRECTION

PATENT NO. : 10,258,932 B2
APPLICATION NO. : 15/124847
DATED : April 16, 2019
INVENTOR(S) : Viola Birss et al.

Page 1 of 1

It is certified that error appears in the above-identified patent and that said Letters Patent is hereby corrected as shown below:

In the Claims

At Column 22, Line 13, Claim 19, replace "and at least on binder" with --and at least one binder--.

Signed and Sealed this
Eighteenth Day of June, 2019

Andrei Iancu
*Director of the United States Patent and Trademark Office*